United States Patent

Hansen et al.

[11] Patent Number: 5,120,546
[45] Date of Patent: Jun. 9, 1992

[54] TRANSDERMAL SYSTEM

[75] Inventors: Jens Hansen, Allerod; Birgitte Mollgaard, Virum, both of Denmark

[73] Assignee: Pharmacia AB, Sweden

[21] Appl. No.: 490,088

[22] Filed: Mar. 7, 1990

[30] Foreign Application Priority Data

Dec. 21, 1989 [SE] Sweden .............................. 8904296

[51] Int. Cl.⁵ .............................................. A61F 13/00
[52] U.S. Cl. ................................... 424/449; 424/448
[58] Field of Search .................. 424/448, 449; 514/58

[56] References Cited

U.S. PATENT DOCUMENTS

| | | | |
|---|---|---|---|
| 4,383,992 | 5/1983 | Lipari | 424/238 |
| 4,596,795 | 6/1986 | Pitha | 514/58 |
| 4,661,105 | 4/1987 | Gale | 604/897 |
| 4,749,574 | 6/1988 | Ueda | 424/448 |
| 4,774,329 | 9/1988 | Friedman | 536/103 |

Primary Examiner—Thurman K. Page
Assistant Examiner—D. Gabrielle Phelan
Attorney, Agent, or Firm—Pravel, Gambrell, Hewitt, Kimball & Krieger

[57] ABSTRACT

The present invention concerns a transdermal system with a reservoir layer comprising an active substance, at least part of which is in the form of an inclusion complex formed between a cyclo compound and the active substance. The release rate from the system is controlled by the dissociation of the complex.

15 Claims, 3 Drawing Sheets

TRANSDERMAL SYSTEM

FIELD OF INVENTION

The present invention concerns a controlled release transdermal delivery system. Specifically the invention concerns a delivery system, from which the release rate of an active substance is governed or controlled by a new principle. The delivery system according to the invention is of particular interest for the transdermal delivery of drugs.

BACKGROUND

Transdermal drug delivery systems can be categorized into three general types. The earliest devices have a simple two-layer "Band-Aid" configuration composed of a backing layer coated with adhesive. Usually the drug is mixed in the adhesive layer that fixes the bandage to the skin. These medicated bandages bring a known quantity of drug to a known area of skin for a known period of time, but have no mechanism for controlling the rate at which the drug is delivered to the patient.

The second type of device, in this context referred to as a monolithic system, is a system incorporating a backing layer, a matrix layer, and an adhesive layer. The matrix layer is made of a polymer material in which the solid drug is dispersed and the rate at which the drug is released from the device is controlled by the polymer matrix. With this type of system, the drug release rate falls off with time as the drug in the skin-contacting side of the matrix is depleted.

This type of transdermal drug delivery system is exemplified by the development and marketing of nitroglycerin-releasing transdermal therapeutic system (Nitro-Dur by Key), which has been approved by the FDA for once-a-day medication of angina pectoris.

The third type of device is the reservoir system. In this case, the drug is contained in a reservoir seperated from the skin by an inert polymeric membrane that controls the rate, at which drug is delivered to the skin. These devices offer an important advantage over the monolithic geometry because as long as the drug solution in the reservoir remains saturated, the drug release rate through the membrane is constant.

The rate of drug release from this type of transdermal drug delivery system can be tailored by varying the polymer composition, the permeability coefficient, and/or the thickness of the rate-controlling membrane and adhesive. Several transdermal therapeutic systems have been successfully developed from this technology and are best exemplified by the development and marketing of a nitro-glycerin-releasing transdermal therapeutic system (Transderm-Nitro by Ciba), which has been approved by the U.S. Food and Drug Administration (FDA) for once-a-day medication of angina pectoris a scopolamine-releasing transdermal therapeutic system (Transderm-Scop by Ciba) for 3-day protection from motion sickness and a clonidine-releasing transdermal therapeutic system.

A fourth type of device is a microreservoir-type drug delivery system. In this approach, the drug reservoir is formed by first suspending the drug solids in the aqueous solution of a water-soluble polymer (e.g. polyethylene glycol) and then dispersing the drug suspension homogeneously in a lipophilic polymer, by high-shear mechanical force, to form thousands of unleachable, microscopic spheres of drug reservoirs. This thermodynamically unstable dispersion is quickly stabilized by immediately cross-linking the polymer chains in situ, which produces a medicated polymer disc with a constant surface area and a fixed thickness. A transdermal therapeutic system is then produced by positioning the medicated disc at the center of an adhesive pad. This technology has been successfully utilized in the development and marketing of a nitroglycerin-releasing transdermal therapeutic system (Nitrodisc by Searle) that has been approved by the FDA for once-a-day treatment of angina pectoris.

The pattern of drug release from the device is important. If drug is delivered to the skin at a rate less than the maximum rate at which it can be absorbed by the skin, the device is the primary dosage controlling mechanism. When drug is delivered to the skin faster than the skin can absorb it, the skin surface is then saturated with drug at all times, and the limiting factor for systemic dosage is the rate of absorption through the skin.

As the skin is substantially impermeable to most drugs the delivery rate is controlled by the skin in most real systems. One approach to solve this problem is to administer a permeation enhancer alongside with the drug. These enhancers can be used in the new system according to the present invention as well as in the old systems.

SUMMARY OF THE INVENTION

According to the present invention the release rate of an active substance, e.g. a drug, from a transdermal system, is controlled by the dissociation of an inclusion complex of the substance in a drug depot. Specifically the active substance in the depot or reservoir is at least partly in the form of an inclusion complex. It is preferred that the cyclo compound according to the invention is a cyclisized polysaccharide. The best known of these compounds and the most preferred ones are the cyclo-dextrins. Derivatives and polymers of cyclodextrins are also of special interest in this connection.

It is previously known to use cyclodextrins in transdermal systems. The most important purposes for which these compounds have been used is to achieve superior properties as to solubility, releasing properties, stability, bioavailability and efficacy of certain active substances, e.g. some steroids (Japanese patent application 113275/1983), 2-nitroxymethyl-6-chloro-pyridine (U.S. Pat. No. 4,749,574) and nitroglycerin (Japanese patent application 81 123912).

It is thus previously known that active substances e.g. drugs can be included in transdermal patches in the form of cyclodextrin complexes for various reasons. To the best of our knowledge, however, it has not been disclosed or suggested that such complexes can be used for controlling the release rate from the system in accorrdance with the present invention.

The new concept of controlling the release rate from a device according to the present invention can be adapted to deliver different active substances at different rates and have no obligatory need for a separate membrane for controlling the release rate of the active substance. Furthermore, the system according to the invention offers several possibilities of tailoring the release rate for a specific active substance. It will thus be possible to obtain a predetermined release rate profile of the active substance from the system according to the invention. In this context a predetermined release rate also includes a substantially constant release rate. These possibilities are of course based on factors which influence the dissociation of the inclusion complex in the surrounding medium.

In the following, the term "controlled release" designates a gradual release at a predetermined time and at a desired rate during a predetermined release period.

According to the present invention the inclusion complex formed between the active drug substance and a cyclodextrin constitutes a drug depot from which the active substance is released in a controlled manner depending on the dissociation of the inclusion complex under the prevailing conditions.

For an inclusion complex in solution, some of the enclosed active substance will be displaced by solvent molecules. The extent thereof will depend on the dissociation constant of the inclusion complex under the prevailing conditions, as, according to the partition behaviour/affinity of the active substance the molecules of the active substance, will distribute between the surrounding medium and the cavity of the cyclo compound. This competitive process determines the amount of active substance molecules present as free molecules and as complex bound molecules, respectively. Active substance present as free molecules will diffuse much easier than the complex bound active substance due to the large difference in molecular size and, thus, the amount of free active substance present is determinative for the release rate of active substance from the transdermal drug delivery system.

For the 1:1 complex the equilibration equation of the dissociation process will be $$CyD-drug \; CyD+drug$$

and hence, the dissociation constant of the complex will be $$Kd = \frac{[CyD] \times [drug]}{[CyD\text{-}drug]}$$

The amount of free active substance present in the transdermal drug delivery system will depend on the size of the dissociation constant and the rate at which the dissociation equilibration is established. Thus the control of the release rate of the active substance from the transdermal drug delivery system is governed by the dissociation of the inclusion complex.

A predetermined dissociation of the inclusion complex will result in a specific drug release profile. According to the invention a desired release rate profile can be achieved by:

1. choice of cyclodextrine, e.g. α-, β- or γ-cyclodextrine, derivatives or polymers thereof.
2. choice of molar ratio of drug to cyclodextrine in the inclusion complex.
3. mixing different cyclodextrine inclusion complexes.
4. adding excess amount of cyclodextrine to the system.
5. adding free drug to the system, i.e. priming dose.
6. adding pH-adjusting agents to the system.
7. adding hydrophilic or lipophilic solvents to the systems.

For economic reasons it has been preferred to use cyclodextrins composed of from 6 to 8 a-1,4.D-glucopyranose units. These cyclodextrins are called α-, β-, and γ-cyclodextrins, respectively, and are preferred cyclo compounds in the context of this invention; especially preferred are the β-cyclodextrins. β-Cyclodextrin consists of seven glucose units and the cavity has an internal diameter of about 7-8 Å.

In this context the term "cyclodextrin polymers" denotes molecules which comprise two or more cyclodextrin units and have a molecular weight exceeding 2000. Preferred cyclodextrin polymers according to the invention are those composed of α-, β- and/or γ-cyclodextrins.

In this context the term "cyclodextrin derivatives" denotes substituted cyclodextrins or substituted cyclodextrin polymers.

Principles and methods for the preparation of cyclodextrin derivatives are well known to a person skilled in the art and are reviewed in e.g. Szejtli, J. "Cyclodextrins and their inclusion complexes", Akademia Kiado, Budapest 1982, pp. 75-81 to which reference is made.

The molar ratio of guest to host in an inclusion complex formed between the active substance and the cyclodextrin is from about 0.1:1 to about 10:1, especially from about 0.2:1 to about 5:1, in particular from about 0.3:1 to about 4:1. The values given are the ratio between the active substance and the cyclo compound monomer. For example for an inclusion complex with a molar ratio of 1:1, one guest molecule is enveloped in one cyclodextrin molecule. If the inclusion complex is formed between a cyclodextrin polymer comprising three cyclodextrin units (three monomeric units) and a guest molecule, a ratio of 1:1 denotes that one molecule of the guest is enveloped per monomeric cyclodextrin unit, i.e. one cyclodextrin polymer molecule will actually host three guest molecules. A stoichiometry of 0.5:1 denotes that two cyclodextrin molecules (calculated as monomeric units) host one guest molecule. This situation may apply when the guest molecule is too bulky to be included in one cyclodextrin cavity, e.g. steroid hormones usually need more than one cyclodextrin molecule for the inclusion. A stoichiometry of e.g. 2:1 is obtained when two guest molecules are situated in one cyclodextrin molecule (calculated as monomeric units). This situation may apply when the guest molecule is much smaller than the cavity in the cyclodextrin molecule. The most common inclusion complexes have a stoichiometry of about 1:1.

The equilibrium between the inclusion complex and the free active substance can be shifted in a direction which favours the existence of the drug-cyclodextrin inclusion complex by adding to the reservoir layer a calculated amount of free cyclodextrin compound and thus decrease the release rate of active substance from the system.

In some cases it is desirable to incorporate a suitable amount of free active substance to obtain a rapid access of the active substance to the skin in order to saturate binding sites in the skin and/or to obtain a prompt therapeutic effect, a so called priming dose.

Agents which can influence the dissociation constant for complexes containing drugs in form of acids/bases include pH adjusting agents. pH adjusting agents are agents which influence the pH in the surrounding medium, e.g. pharmaceutically acceptable salts such as alkali metal and alkaline earth metal salts and buffer substances such as acetate, citrate, phosphates, tartrates, bicarbonates and carbonates etc.

Other agents which may influence the dissociation of the inclusion complex include hydrophilic and/or hydrophobic solvents. Examples of hydrophilic solvents include polyols such as propylene glycol, polyethylene glycols, glycerol and the like, and examples of hydrophobic solvents include fatty acid glycerides such as miglyol, fatty acid esters such as isopropyl myristate, polysorbates etc., liquid paraffin, silicone fluid and the like and mixtures thereof.

In the present context the term "trandermal delivery system" encompasses systems that are applied onto the surface of intact, damaged or diseased skin of a mammal, in particular a human, for the purpose of delivering an active substance to the skin to obtain a localized effect on the skin or in the skin, to obtain a systemic effect after entry of the active substance in the circulatory system through the skin or to obtain an effect via the lymphatic system.

Accordingly, the invention relates to a transdermal delivery system in the form of a multilaminar device to be applied on the skin of a mammal for controlled release of an active substance to the mammal, comprising the following layers:

A) at the skin-distal side, a backing membrane which is substantially impermeable to the active substance, B) optionally one or more layers of adhesive, optionally comprising an active substance, C) a reservoir layer comprising an active substance and optionally an adhesive agent, D) optionally a protecting membrane situated adjacent to the reservoir layer opposite to the backing membrane, and E) a release liner at the side of the device to be applied to the skin, which release liner is adapted to be removed prior to use.

A transdermal delivery system according to the invention comprises one or more active substances. The active substance may be present in one or more layers or laminas of adhesive and/or be present in a reservoir layer or lamina comprising the active substance as a depot. At least part of the active substance is in the form of an inclusion complex formed between the active substance and a cyclo compound.

The active substance or substances included in the delivery system of the invention may be selected from many therapeutic groups including antiinflammatory drugs (e.g. ibuprofen, indomethacin, naproxen, diclofenac, tolfenamic acid, piroxicam), analgesics (e.g. buprenorphine, codeine, fentanyl, morphine, hydromorphone), tranquilizers (e.g. diazepam, droperidol, fluspirilene, haloperidol, lorazepam, cardiac glycosides (e.g. digoxin, ouabain), narcotic antagonists (e.g. naloxone, nalorphine), antiparkinsonism agents (e.g. bromocriptine, biperiden, benzhexol, benztropine), antidepressants (e.g. imipramine, nortriptyline, protriptylene), antineoplastic agents and immunosuppressants (e.g. belomycin, cyclosporin A, fluorouracil, mercaptopurine, methotrexate, mitomycin), antiviral agents (e.g. idoxuridine, acyclovir, interferons, vidarabin), antibiotic agents (e.g. clindamycin, erythromycin, fusidic acid, gentamicin), appetite suppressants (e.g. fenfluramine, mazindol, phentermin), antiemetics (e.g. metoclopramide, droperidol, haloperidol, promethazine), antihistamines (e.g. chlorpheniramine, terfenadine, triprolidine), antimigraine agents (e.g. dihydroergotamine, ergotamine, pizotyline), coronary, cerebral or peripheral vasodilators (e.g. nifedipine, diltiazem), antianginals (e.g. glyceryl trinitrate, isosorbide dinitrate, molsidomine, verapamil), calcium channel blockers (e.g. verapamil, nifedipine, diltiazem, nicardipine), hormonal agents (e.g. estradiol, estron, estriol, polyestradiol, polyestriol, dienestrol, diethylstilbestrol, progesterone, dydrogesterone, cyproterone, danazol, testosterone), contraceptive agents (e.g. ethinyl estradiol, lynestrenol, etynodiol, norethisterone, mestranol, norgestrel, levonorgestrel, desogestrel, medroxyprogesterone), antithrombotic agents (e.g. heparin, warfarin), diuretics (e.g. hydrochlorothiazide, flunarizine, minoxidil), antihypertensive agents (e.g. propanolol, metoprolol, clonidine, pindolol), chemical dependency drugs (e.g. nicotine, methandone), local anaesthetics (e.g. lidocaine, prilocaine, benzocaine), corticosteroids (e.g. beclomethasone, betamethasone, clobetasol, desonide, desoxymethasone, dexamethasone, diflucortolone, flumethasone, fluocinolone acetonide, fluocinonide, hydrocortisone, methylprednisolon, triamcinolone acetonide, budesonide, halcinonide), dermatological agents (e.g. nitrofurantoin, dithranol, clioquinol, hydroxyquinoline, isotretinoin, methoxsalen, methotrexate, tretinoin, trioxsalen, salicylic acid, penicillamine), and the like.

Examples of specific active substances are steroids such as estradiol, progesterone, norethindrone, levonorgestrol, ethynodiol, levenorgestrel, norgestimate, gestanin, desogestrel, 3-keton-desogestrel, demegestone, promethoestrol, testosterone, spironolactone, and esters thereof; a nitro compound such as amyl nitrates, nitroglycerine and isosorbide nitrates; an amine compound such as prilocaine, oxybutyninchloride, lidocaine, benzocaine, nicotine, chlorpheniramine, terfenadine, triprolidine, propanolol and metoprolol; an oxicam derivative such as piroxicam; a mucopolysaccharide such as thiomucase; an opioid such as morphine and morphine-like drugs such as buprenorphine, oxymorphone, hydromorphone, levorphanol, fentanyl and fentanyl derivatives and analogs; a prostaglandin such as a member of the PGA, PGB, PGE and PGF series, such as e.g. misoprostol and enaprostil; a benzamide such as metoclopramide and scopolamine; a peptide such as growth-hormone releasing factors, growth factors (EGF, TGF, PDGF and the like), somatostatin and insulin; a xanthine such as caffeine and theophylline; a catecholamine such as ephedrine, salbutamol and terbutaline; a dihydropyridine such as nifedipine; a thiazide such as hydrochlorothiazide and flunarizine; a sydnonimine such as molsidomine; and a sulfated polysaccharide such as heparin.

The active substance present in the transdermal delivery system in form of an inclusion complex or as a free, non-complex bond active substance can be in various forms, such as unchanged molecules, molecular complexes, or a pharmaceutically acceptable salt such as a hydrochloride, hydrobromide, sulfate, laurylate, palmitate, phosphate, nitrite, nitrate, borate, acetate, maleate, tartrate, oleate and salicylate. For acidic active substances, salts of alkali metals, such as sodium or potassium, alkaline earth metals, such as magnesium or calcium, amines, amino acids, organic cations or quaternary ammonium can be used. Furthermore, the free or inclusion complex bond active substance in the transdermal delivery system can also be in the form of an ester, ether or amide, which prior to or after their release from the delivery system can be converted by enzymes, hydrolyzed by action of body water at a physiologically relevant pH or other metabolic processes to the original form or to a biologically active form. Such bioreversible derivatives which are substantially inactive per se are denoted prodrugs.

The cyclodextrin inclusion complexes can be prepared according to methods well known to a person skilled in the art. The most common procedures comprise stirring or shaking of an aqueous solution of the particular cyclodextrin with the guest substance or a solution thereof. The reaction is preferably carried out in a common solvent like water, or in different but miscible or immiscible solvents, or in no solvent at all, at acidic or neutral pH and at low, ambient or elevated temperature. After an equilibrium is reached, the solvent can be removed by filtration and subsequent oven-, vacuum-, freeze- or spray-drying, or the solvent is removed by any other suitable method well known to a person skilled in the art.

For drugs, which cannot be administered transdermally at a rate high enough to achieve a therapeutic blood level it is required to involve methods to reduce the skin's barrier properties. Two approaches of enhancing the permeation of drug can be used; bioconvertible prodrugs and penetration enhancers.

Prodrugs can be viewed as the therapeutically inactive derivatives of a therapeutically active drug that undergo bioconversion, either by chemical or enzymatic transformation, in a biological environment, to regenerate the therapeutically active parent drug prior to exhibiting their pharmacological activities.

The prodrug concept can be applied in transdermal controlled drug delivery by altering skin permeability via modification of the physicochemical properties of the drug molecule to enhance its rate of transdermal permeation.

Prodrugs of a poorly skin-permeable drug may be synthesized to improve percutaneous absorption characteristics. During the course of transdermal permeation, the prodrugs can be transformed, by the drug. In other words, if an active drug has a rather low affinity toward the skin, it will not easily partition into it to any great extent. The partition behaviour of such a drug can be improved by a simple chemical modification to form a lipophilic prodrug. Upon absorption and penetration through the skin, the prodrug is rapidly metabolized to regenerate the active parent drug. One typical example of this approach is the esterification of less skin-permeable estradiol to form lipophilic estradiol esters e.g. estradiol-17-acetate and estradiol-3,17-diacetate.

Skin penetration enhancers are compounds which can improve the skin permeability of drugs. The transdermal drug delivery systems release one or more skin permeation enhancers to the surface of the stratum corneum to modify the barrier properties of the skin before the controlled delivery of the active drug, and to render the skin more permeable to the drug. The enhancers should be incorporated into the drug depot layer and/or the layer of adhesive of the transdermal delivery system. One or more penetration enhancers may be present in the transdermal delivery system.

Some representative classes of potential skin penetration enhancers are:
alkyl methyl sulfoxides, e.g. decylmethyl sulfoxide, dimethyl sulfoxide;
saturated fatty acids and alkyl esters thereof, e.g. caproic acid, caprylic acid, capric acid, myristic acid, lauric acid, stearic acid, palmitic acid;
unsaturated fatty acids and alkyl esters thereof, e.g. oleic acid, linoleic acid, linolenic acid, palmitoleic acid;
saturated fatty alcohols, e.g. myristyl alcohol, lauryl alcohol, stearyl alcohol, palmityl alcohol, cetyl alcohol;
unsaturated fatty alcohols, e.g. oleyl alcohol, palmitoleyl alcohol, elaidyl alcohol, linoleyl alcohol, linolenyl alcohol;
azocyclo-alkan-2-ones, e.g. 1-dodecylazacycloheptan-2-one (Azone TM);
pyrrolidones, e.g. 2-pyrrolidone, alkyl-2-pyrrolidone, N-methylpyrrolidone;
glycols, e.g. propylene glycol, polyethylene glycols, glycerol, dipropylene glycol, tripropylene glycol, diethylene glycol, triethylene glycol;
alcohols, e.g. ethanol, isopropyl alcohol, cyclohexanol;
others, e.g. diethyltoluamide, tetrahydrofurfuryl alcohol, dimethyl formamide, dimethyl acetamide, 2,2,2-trichloroethanol, 2,2,2-trifluoroethanol, urea, salicylic acid, ethylene glycol monomethyl ether, N,N-dialkylhydroxylamine, 1,2-isopropylidene glycerol, N,N-dialkylnicotinamide, alkylaminooxide, hyaluronidase, isopropyl myristate, saccharose monooleate, lecithins, non-ionic surfactants, cholic acid and derivatives thereof.

According to the present invention, the active substance is present in a reservoir layer of the delivery system. Suitable reservoir layer materials are materials which do not influence the active substance in any unappropriate way so as to e.g. decrease the mobility of the active substance in the reservoir layer. In the specification and claims, the term "reservoir layer" designates any type of layer which serves as a drug reservoir layer.

Thus the reservoir layer may comprise a solid polymer matrix in which the inclusion complex may be dispersed.

The reservoir layer may also comprise a viscous polymer matrix in which the inclusion complex is incorporated to form a cream-like suspension.

If the reservoir layer is fluid, the layer is normally covered by a protective membrane to keep the integrity of the system, said protective membrane having substantially no influence on drug release from the system. A flexible layer of adsorbent material can give structure to the reservoir layer. The materials is preferably of a non-wowen fabric, e.g. polyester, polyethylene, polypropylene or polyamides. Wowen fabrics, however, can also be used if desired.

Examples of suitable matrix materials including semisolid materials are those selected from the group consisting of cellulose derivatives such as cellulose esters [cellulose acetate, cellulose acetate butyrate (Rabisan TM), cellulose acetate phthalate (Eastman C A P)], cellulose nitrates (Collodium), cellulose ethers [carboxymethyl cellulose (Cellogel C TM, Cellosan TM), ethyl cellulose (Ethocel ™), hydroxyethyl cellulose (Cellosize Polymer PCG-10 ™, -HEC ™), hydroxypropyl cellulose (Klucel), methyl cellulose (Methocel ™, Tylosen ™), methylethyl cellulose (Cellofas A ™), methyl hydroxypropyl cellulose (Celacol HPM)], polyethylene glycol, cellulose polymer (Alcoramnosan ™, Idroramnosan ™), polyvidones (Kollidon ™, Periston ™), alginates (Kelcoalginate ™, Kelcogel ™, Kelcosol ™, Kelgine ™, Kelmar ™, Keltone ™, Manucol-Ester ™, Protanal ™, Protatek ™), polyacrylic acids (Carbomer, Carbopol), polyacrylates (Permasorb ™, Acronal ™), polyacrylamides (Cyanamer ™, Gelamide ™), poloxamer (Pluronics ™), gelatines (Pharmagel A, Thiogel ™), polyvinyl alcohols (Elvanol ™, Gelvatol ™, Lemol ™, Polyviol, Vinylon), polyvinylacetates (Mowilith ™, Vinnapas ™), pectines, pectine amides, polyethylene glycols (Carbowax ™, Carbox ™, Dow Polyglycols ™), dextranes (Macrodex ™, Rheomacrodex ™), silicones (Dow Corning ™ 470A, 471A, GE-Silicones ™, Polysiloxanes), carrageen (Santiagel ™, Santiagum ™), silica (Veegum ™, Ludox ™, colloidal silica, Macoloid ™), polyoxyethylene-polyoxypropylene block polymers (Poloxamine, Tetronic ™), methylvinyl ether-maleic acid anhydride copolymer (Viscofas ™), karaya gums (Sterculia gum, Indian tragacanth), tragacanth (Gum Dragon ™, Tragant ™), xanthan gums (XB-23 biopolymer), polystyrenes (Polystyrol LG, Litex ™), styrene-butadiene copolymer (Ameripol ™, Austrapol ™, Duradene ™, Synapren ™), polyvinyl chloride (Lutofan ™, Rhenoflex ™, Vinnol ™), polyvinylidene chloride (Diafan ™), polyethylenes (Aldurol ™, Celipal ™, Ludopal ™, Dynapol ™), polypropylenes (Alprodur ™), polysulfones (Udel, Sulfil ™), polyisobutylenes (Oppanol ™, Luvitol ™) polyisobutenes (Parleam ™), polyurethanes (Beckocoat ™, Desmodur ™).

Backing membrane is preferably made of a sheet or film that is substantially impermeable to the selected drug. The layer is preferably on the order of 10 to 75 microns in thickness, and may or may not contain pigment. The layer is preferably of a material that permits the device to mimic the contours of the skin and be worn comfortably on areas of skin, such as at joints or other points of flexure, that are normally subjected to mechanical strain with little or no likelihood of the device disengaging from the skin due to differences in the flexibility or resiliency of the skin and the device. Examples of polymers that are useful are polyether block amide copolymers (e.g., PEBAX copolymers), polyethylene methyl methacrylate block copolymers (EMA) such as NUKRELL polymers, polyurethanes such as PELLATHANE or ESTANE polymers, silicone elastomers, polyester block copolymers that are composed of hard and soft segments (e.g. HYTREL polymers), rubber-based polyisobutylene, styrene, and styrene-butadiene and styreneisoprene copolymers. Other polymers that may be used include polyethylene, polypropylene, polyesters, e.g., polyester terephthalate (PET), which may be in the form of films or laminates. The preferred polymer used for the backing will depend on the material or drug incorporated into the device and on the nature of any vehicles, solubilizers, or the like that are used.

Examples of suitable materials for adhesive layer include polysiloxanes, polyisobutylenes, polyacrylates, polyurethanes, plasticized ethylene-vinyl acetate copolymers, low molecular weight polyether block amide copolymers (PEBAX copolymers), tacky rubbers such as polyisobutene, polystyrene-isoprene copolymers, polystyrene-butadiene copolymers, and mixtures thereof. Mixtures of polyisobutylenes and polyisobutenes are preferred. The thickness of the anchor adhesive layer may vary, but is typically in the range of about 10 to about 125 microns.

The function of the protective membrane is only to protect the drug depot and the passage of this should not contribute to the controlled release of drugs from the transdermal system. Examples of plastic materials: polystyrene, styrene-butadien copolymer, polyvinyl chloride, polyethylene, polypropylene, polysulfone, cellulose esters, polyvinylidene fluoride, ethylen-vinylacetat-copolymer.

Prior to use, the transdermal system includes a release liner. Just prior to use, this layer is removed from the system to expose the contact adhesive layer. The release liner will normally be made from a drug/vehicle/enhancer impermeable material that is inherently "strippable" or rendered so by techniques such as silicone or fluorocarbon treatment.

The following examples further illustrate the invention. They are not intended to limit the invention in any way. Unless indicated otherwise proportions are by weight.

Materials and apparatus used in the examples

Materials

Cinnamyl alcohol, Zimtalkohol zur Synthese, Merck-Schuchardt: Cinnamyl alcohol is used as a model substance. Nicotine, (−)-Nicotin zur Synthese, Merck-Schuchardt Polyvidon 90, polyvinyl pyrrolidone, BASF Propylene glycol, Ph. Eur. 2nd Ed.
Liquid paraffin, Paraffinum liquidum, Ph. Eur. 2nd Ed.
Hexane, n-Hexan z.A., Merck
Acronal V 205, BASF
355 Medical Adhesive, Dow Corning
Oppanol 10, BASF
Oppanol 50, BASF
Oppanol 120, BASF
$\beta$-cyclodextrin, ($\beta$-CD), Avebe
$\beta$-cyclodextrin inclusion complexes of cinnamyl alcohol ($\beta$-CD-CA) and nicotine ($\beta$-CD-N) were prepared in our laboratory.
Backing membrane: Polyester sheet, Mylar type D, Dupont
Release liner: Siliconized polyethylene (HDPE) foil, 4P Folie Forchheim GmbH.

Apparatus

Equipment for corona treatment: Vetaphone Elektronik A/S, Kolding, Denmark
Coating equipment: RK Print Coat Instrument Ltd., Littington, Great Britain, Type KCC 202, K-contol coater bar: No 7
Drying equipment: The drying equipment is constructed by Pharmacia.
Spectrophotometer: LKB Ultrospec ™ II

EXAMPLE 1

Preparation of inclusion complex of $\beta$-CD and nicotine ($\beta$-CD-N).

100 g water were heated to 75° C. 28 g of $\beta$-CD were added and dissolved while stirring the solution. 3.5 ml of nicotine were added. The mixture was stirred for

EXAMPLE 2

Preparation of inclusion complex of β-CD and cinnamyl alcohol (β-CD-CA).

227 g β-CD were dissolved in 1750 ml water while stirring and heating to 70° C. 26.83 g melted cinnamyl alcohol were added. The mixture was stirred for about 2 h at ambient temperature. The obtained mixture was filtered and dried in a drying oven at room temperature.

EXAMPLE 3

Preparation of polyvidon 90 gel for use in the reservoir layer

Composition:
Ethanol 99.9% 226 g
Dem. water 200 g
Polyvidon 90 125 g

Ethanol and water were mixed and polyvidon 90 was added gradually while stirring. The stirring was continued in further 10 minutes, after which the gel was left to swell for at least 16 h.

EXAMPLE 4

Composition of adhesive preparations

I A polyisobutylene-type:
Oppanol 10 1.0 g
Oppanol 50 1.5 g
Oppanol 120 2.0 g
Hexane 30.0 ml
Liquid paraffin 5.5 g II An acrylic-type: Acronal V 205, BASF, which according to the supplier is a dispersion of acrylic copolymers in water.

III A silicone-type: 355 Medical Adhesive, Dow Corning. Composition according to the supplier: 18.5% dimethylpolysiloxane by weight in trichlorotrifluorethane.

EXAMPLE 5

Figure 1:
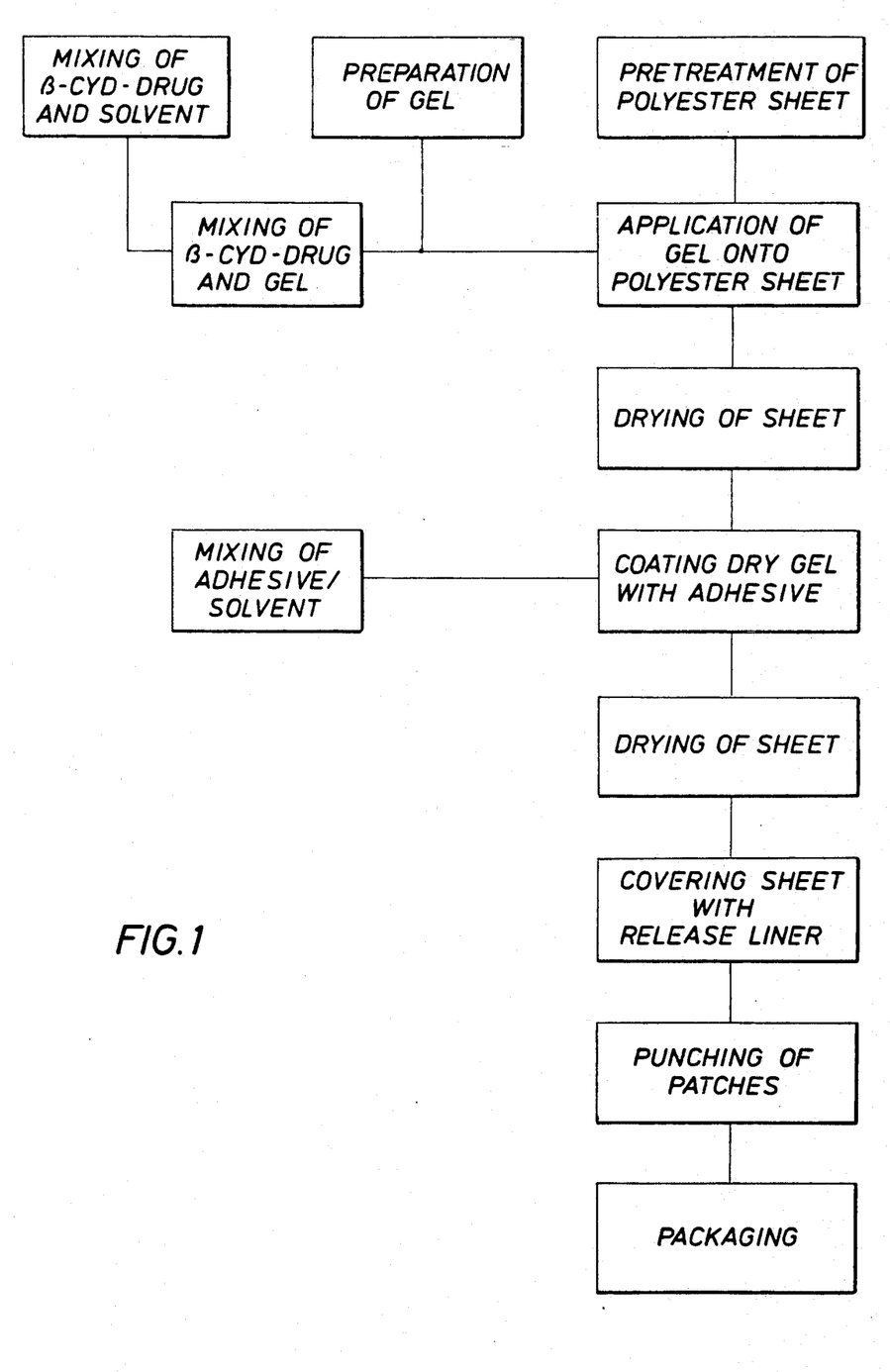
FIG. 1 is a flow chart showing procedures for manufacturing transdermal drug delivery systems according to the invention.

The general manufacturing procedures for preparing transdermal drug delivery systems are outlined in FIG. 1.

In order to secure good attachment of the drug reservoir layer to the backing membrane the polyester sheets to become the backing membrane were exposed for corona treatment immediately before application of the drug gel.

The volatile solvents were evaporated from the gel coated sheets and the adhesive coated sheets by placing the sheets in a drying oven working according to the following principle; cleaned fresh air was blown onto the wet sheets by means of a propellar. The drying air, loaded with solvent, was exhausted.

EXAMPLE 6

Transdermal drug delivery systems with cinnamyl alcohol as the active substance.

System 1

16 g β-CD-CA was suspended in 16 g dem. water and the suspension was added to 15 g polyvidon 90 gel (example 3) to give the drug gel. The drug gel was solvent cast onto a polyester sheet 75 μm thick by means of the coating machine in a thin layer (70 μm). After drying at room temperature adhesive preparation I (example 4) was solvent cast onto the gel coated sheet and subsequent drying at room temperature.

The adhesive layer was covered by the release liner and the sheets were kept at 8° C. until use.

The resulting sheet with backing membrane, reservoir layer and adhesive layer was 120 μm thick. The concentration of cinnamyl alcohol was determined according to example 8 to 0.15 mg cinnamyl alcohol per cm$^2$.

System 2

16 g β-CD-CA was suspended in 5 g propylene glycol mixed with 11 g dem. water. The suspension was added to 15 g polyvidon 90 gel (example 3) to give the drug gel. The drug gel was solvent cast onto a polyester sheet 75 μm thick by means of the coating machine in a thin layer (70 μm). After drying at room temperature adhesive preparation I (example 4) was solvent cast onto the gel coated sheet and subsequent drying at room temperature.

The adhesive layer was covered by the release liner and the sheets were kept at 8° C. until use.

The resulting sheet with backing membrane, reservoir layer and adhesive layer was 128 μm thick. The concentration of cinnamyl alcohol was determined according to example 8 to 0.16 mg cinnamyl alcohol per cm$^2$.

System 3

2.0 g cinnamyl alcohol was added to 32.0 g polyvidon 90 gel (example 3) to give the drug gel. The drug gel was solvent cast onto a polyester sheet 75 μm thick by means of the coating machine in a thin layer (70 μm). After drying at room temperature adhesive preparation I (example 4) was solvent cast onto the gel coated sheet and subsequent drying at room temperature.

The adhesive layer was covered by the release liner and the sheets were kept at 8° C. until use.

The resulting sheet with backing membrane, reservoir layer and adhesive layer was 112 μm thick. The concentration was determined according to example 8 to 0.45 mg cinnamyl alcohol per cm$^2$.

Figure 2:
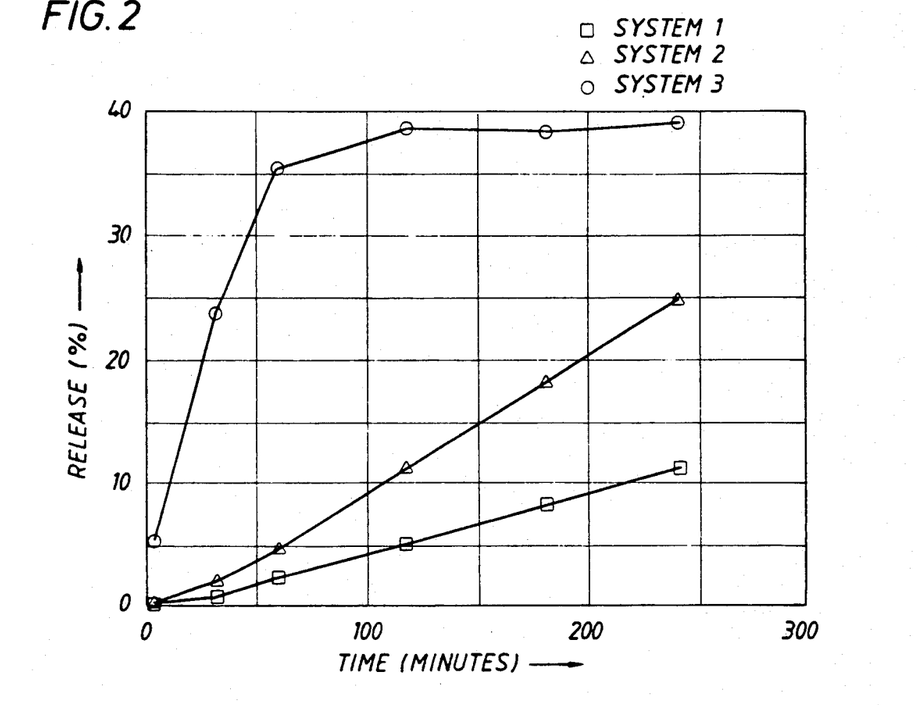
FIG. 2 graphically depicts release of cinnamayl alcohol from the transdermal drug delivery system of example 6; systems 1, 2, and 3.

In vitro release studies according to example 9 were carried out on the systems 1, 2 and 3 described above. The results of these studies are reported graphically in FIG. 2. From system 1 which comprises β-cyclodextrin inclusion complex of cinnamyl alcohol in the reservoir layer cinnamyl alcohol is released slowly with a constant rate of 4.37 μg cm$^{-2}$h$^{-1}$. From system 2 which comprises β-cyclodextrin inclusion complex of cinnamyl alcohol and propylene glycol in the reservoir layer cinnamyl alcohol is released with a somewhat higher constant rate of 7.91 μg cm$^{-2}$h$^{-1}$. As shown, both system 1 and 2 revealed approximately zero order release kinetics. For comparison purposes release studies were carried out on system 3 which comprises neat cinnamyl alcohol without β-cyclodextrin in the reservoir layer. System 3 revealed a curvelinear profile and the active substance was released very fast as about 40% of the dose is released in about 100 minutes.

Thus in conclusion, β-cyclodextrin inclusion complexes as drug depots control the release of active substance and by adding solvents, e.g. propylene glycol, to the surrounding medium in the reservoir layer it is possible to influence the release rate.

System 4

16 g β-CD-CA was suspended in 16 g dem. water, and the suspension was added to a mixture of 7.5 g polyethylene glycol 400 and 10.5 g polyethylene glycol 6000 to give the drug gel. The drug gel was solvent cast onto a polyester sheet 75 μm thick by means of the coating machine in a thin layer (70 μm). After drying at room temperature adhesive preparation III (example 4) was solvent cast onto the gel coated sheet and subsequent drying at room temperature.

The adhesive layer was covered by the release liner, and the sheets were kept at 8° C. until use.

The resulting sheet with backing membrane, reservoir layer and adhesive layer was 136 μm thick. The concentration of cinnamyl alcohol was determined according to example 8 to 0.14 mg per cm$^2$.

In vitro release studies according to example 8 were carried out on system 4 described above. The release profile was substantially similar to that obtained for system 1, FIG. 2.

System 5

16 g β-CD-CA was suspended in 16 g adhesive preparation II (example 4) mixed with 1.5 g dem. water to give the drug gel. The drug gel was solvent cast onto a polyester sheet 75 μm thick by means of the coating machine in a thin layer (70 μm), and subsequent drying at room temperature.

The reservoir layer which also is the adhesive layer was covered with the release liner, and the sheets were kept at 8° C. until use.

The resulting sheet with backing layer and reservoir-/adhesive layer was 97 μm thick. The concentration of cinnamyl alcohol was determined according to example 8 to 0.25 mg cinnamyl alcohol per cm$^2$.

Figure 3:
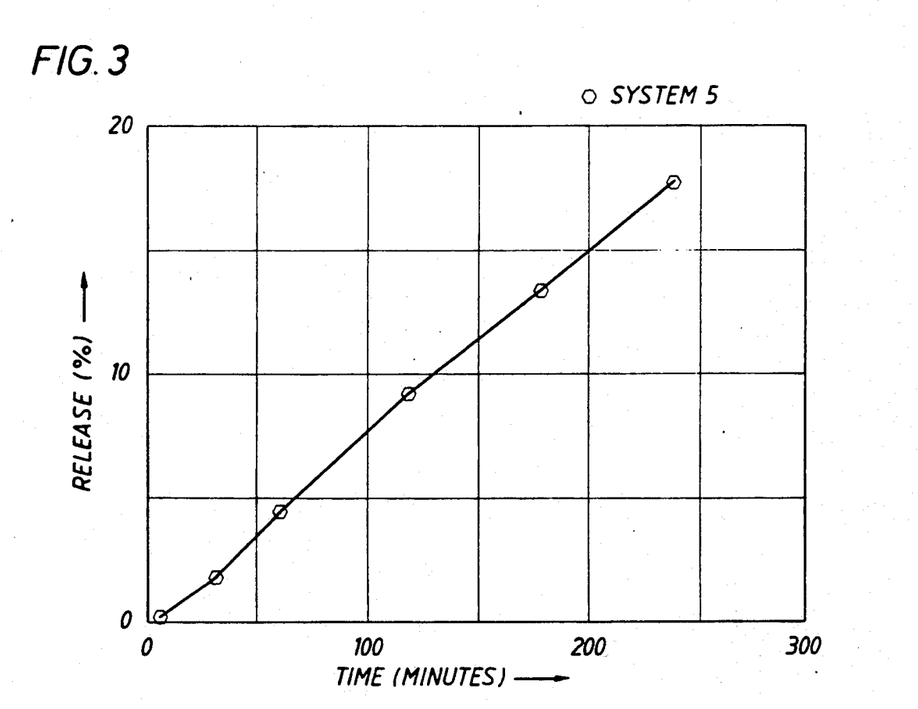
FIG. 3 graphically depicts the release of cinnamayl alcohol from the transdermal drug delivery system of example 6; system 5.

In vitro release study according to example 9 was carried out on system 5 described above. The result of the study is reported graphically in FIG. 3. As shown, system 5 revealed approximately zero order release kinetics with a release rate of 11.19 μg cm$^{-2}$h$^{-1}$.

EXAMPLE 7

Transdermal drug delivery system with nicotine as the active substance.

System 6

3 g β-CD-N was suspended in 2.8 g dem. water mixed with 190 mg propylene glycol. The suspension was added to 2.8 g polyvidon 90 gel (example 3) to give the drug gel. The drug gel was solvent cast onto a polyester sheet 75 μm thick by means of the coating machine in a thin layer (70 μm). After drying at room temperature adhesive preparation II (example 4) was solvent cast onto the gel coated sheet and subsequent drying at room temperature.

The adhesive layer was covered by the release liner, and the sheets were kept at 8° C. until use.

The resulting sheet with backing layer, reservoir layer and adhesive layer was 119 μm thick. The concentration of nicotine was determined according to example 8 to 0.4 mg nicotine per cm$^2$.

System 7

1000 μl nicotine and 400 μl propylene glycol were added to 12.6 g polyvidon 90 gel (example 3) to give the drug gel. The drug gel was solvent cast onto a polyester sheet 75 μm thick by means of the coating machine in a thin layer (70 μm). After drying at room temperature adhesive preparation II (example 4) was solvent cast onto the gel coated sheet and subsequent drying at room temperature.

The adhesive layer was covered by the release liner, and the sheets were kept at 8° C. until use.

The resulting sheet with backing layer, reservoir layer and adhesive layer was 109 μm thick. The concentration of nicotine was determined according to example 8 to 0.2 mg nicotine per cm$^2$.

Figure 4:
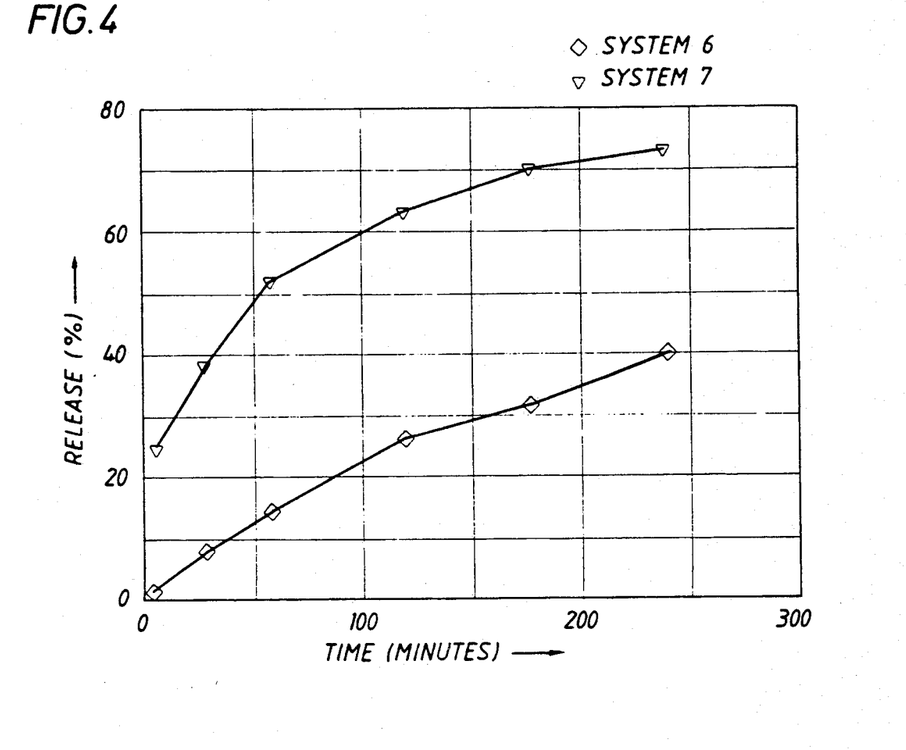
FIG. 4 is a graphic depiction of the release of nicotine from the transdermal drug delivery system of example 7; systems 6 and 7.

In vitro release studies according to example 9 were carried out on the systems 6 and 7 described above. The results of those studies are reported graphically in FIG. 4. From system 6 which comprises β-cyclodextrin inclusion complex of nicotine in the reservoir layer nicotine is released with a slower rate than from system 7 which comprises neat nicotine without β-cyclodextrin in the reservoir layer. As shown, the release rate of nicotine from system 6 declined slightly over the period but more closely approximated zero order release than first order release.

EXAMPLE 8

Quantitative determination of the active substance content in the transdermal drug delivery systems.

Patches of 0.63 cm$^2$ were punched out and extracted with 5.00 ml ethanol in the case of cinnamyl alcohol, and 5.00 ml 0.01N HCl in the case of nicotine. The extracted amount of active substance was determined by UV-spectrophotometry (λmax. (cinnamyl alcohol)=251 nm, λmax. (nicotine)=260 nm), and the concentration of the systems was expressed in mg active substance per cm$^2$.

EXAMPLE 9

In vitro release studies of the transdermal drug delivery systems.

The diffusion cell used consisted of a 24 mm diameter Millipore cellulose ester GSWP type filter mounted on the detachable end of a stainless steel cylinder using silicone glue, thereby dividing the cell into two compartments: a donor and a larger stirred receptor compartment.

Patches of 1.54 cm$^2$ were punched out and mounted on the Millipore filter. The diffusion of the active substance from the upper compartments was followed at room temperature by removing samples periodically and measuring the concentration of the drugs. The receptor phase was 15.00 ml 0.01N HCl in the studies with nicotine and 15.00 ml phosphate buffer 0.05M pH 7.4 in the studies with cinnamyl alcohol.

The amount of active substance in the samples was determined by UV-spectrophotometry according to example 8.

EXAMPLE 10

In vitro permeation from transdermal drug delivery system with nicotine as the active substance.

System 8

18.0 g β-CD-N was suspended in 40.0 g dem. water. The suspension was added to 26.0 g polyvidon 90 gel (example 3) whereafter 6.0 g propylene glycol was added to give the drug gel. The drug gel was solvent cast onto a polyester sheet 75 μm thick by means of the coating machine in a layer of 1.0 mm and the gel layer was dried at room temperature. Adhesive preparation I (example 4) was solvent cast onto a siliconized polyethylene foil and after drying laminated onto the gel coated sheet by means of a steel cylinder (5.5 kg).

The adhesive layer was covered by a release liner (Perlastic TM -L36, PETP-Folie) and the sheets were kept in heat-sealed pouches (Barex TM , polyacrylnitrit-/aluminium-laminate) at 8° C. until use.

The resulting sheet with backing layer, reservoir layer and adhesive layer was 0.5 mm thick and the concentration of nicotine was determined according to example 8 to 1.4 mg cm$^{-2}$.

In vitro permeation of nicotine from transdermal system 8 across human epidermis was investigated with Franz diffusion cells.

Epidermis was heat separated from full thickness human skin and mounted in glass diffusion cells with an available diffusion area of 1.8 cm$^2$. Patches of 1.54 cm$^2$ of system 8 was punched out and applied on the skin surface and the dermal side of the skin was exposed to 12.1 ml recipient phase, 0.01M acetate buffer solution of pH 4.

Figure 5:
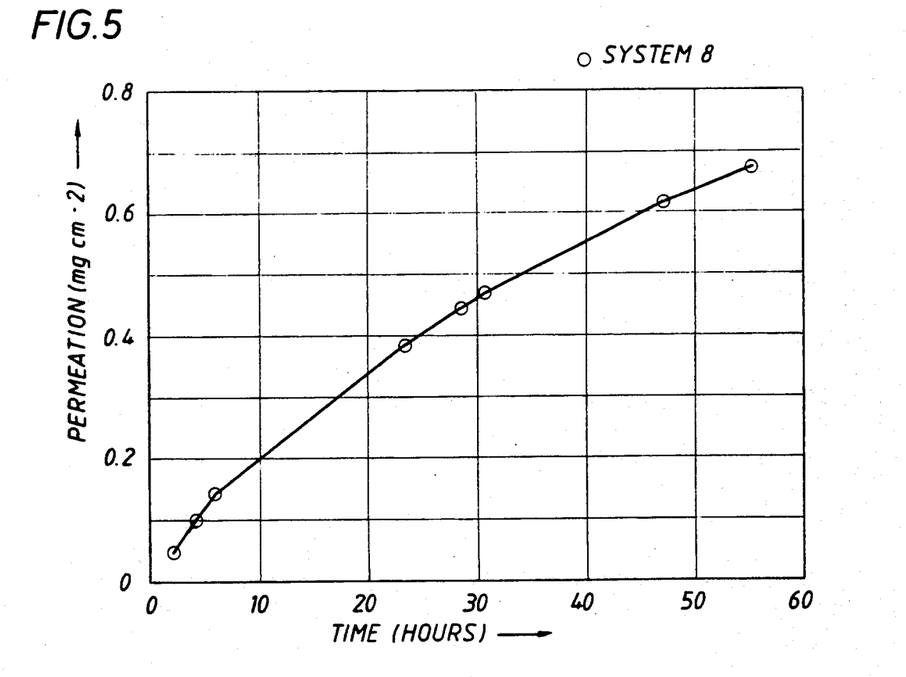
FIG. 5 is a graphic depiction of permeation of nicotine through human epidermis from the transdermal drug delivery system of example 10; system 8.

Permeation of nicotine was followed by removing samples periodically and measuring the concentration by a HPLC method according to example 11. The cumulative amount of nicotine appearing in the recipient phase versus time are shown in FIG. 5. As it appears, system 8 revealed approximately zero order permeation kinetics although the permeation rate of nicotine declined slightly over the period. The initial permeation rate was calculated to 22.2 $\mu$g cm$^{-2}$h$^{-1}$.

EXAMPLE 11

Quantitative determination of nicotine content in the recipient phase samples from skin permeation studies was done by a HPLC method. A LKB system comprising a LKB 2249 HPLC pump, a LKB 2141 variable wavelength monitor, a LKB 2221 integrator and a LKB 2157 autosampler (20 ul injected) was used. The column used, 12 cm long and 4 mm i.d., was packed with Nucleosil 5 CN. The column was eluted isocratically at ambient temperature with a mobile phase consisting of dem. water-acetonitril-diethylamine (400:100:0.38 v/v). The flow rate was 1.0 ml/min. and the column effluent was monitored at 254 nm.

We claim:

1. A transdermal system with a reservoir layer comprising:
   an active substance;
   a cyclized polysaccharide selected from the group consisting of cyclodextrin, cyclodextrin derivative, and cyclodextrin polymer, at least a part of which is in the form of an inclusion complex formed between the cyclized polysaccharide and the active substance, wherein the release of the active substance from the transdermal system is regulated by controlled dissociation of the inclusion complex within said reservoir; and
   optionally, an agent which regulates the controlled dissociation of the inclusion complex within the reservoir, the agent being selected from the group consisting of: excess cyclodextrin, excess free substance, pH adjusting agents, hydrophilic solvents, lipophilic solvents, and mixtures thereof.

2. A transdermal system according to claim 1, wherein the release of the active substance is controlled by manipulation of the contents of the reservoir to influence dissociation of the inclusion complex.

3. A transdermal system according to claim 1, wherein the release rate of the active substance is substantially constant.

4. A transdermal system according to claim 1, wherein the system is in the form of a multilaminar device comprising the following layers:

a) at the skin-distal side, a backing membrane, which is substantially impermeable to the active substance;

b) optionally, one or more layers of adhesive, optionally comprising the active substance;

c) a reservoir layer comprising the active substance and optionally, an adhesive agent, and d) optionally, a protecting membrane situated adjacent to the reservoir layer opposite to the backing membrane; and e) a release liner situated at the side to be applied to the skin, which release liner is removed prior to use.

5. A transdermal system according to claim 1, wherein the system also comprises a permeation enhancer.

6. A transdermal system according to claim 1, wherein the cyclisized polysaccharide is a cyclodextrin.

7. A transdermal system according to claim 1, wherein the active substance is selected from the group consisting of steroids, amyl nitrates, nitroglycerine, isosorbide nitrates, prilocaine, oxybutyninchloride, lidocaine, benzocaine, nicotine, chlorpheniramine, terfenadine, triprolidinee, propanol, metroprolol, oxicam derivatives, opioids, prostaglandines, benzamides, peptides, xanthines, catecholamines, dihydropyridines, thiazides, sulfated polysaccarides and mucopolysaccaraides.

8. A transdermal system according to claim 7, wherein the drug is nicotine.

9. A transdermal system according to claim 7, wherein the drug is estradiol.

10. A method of controlled drug delivery comprising administering to the skin of a patient a transdermal system according to claim 1.

11. A method of controlled drug delivery comprising administering to the skin of a patient a transdermal system according to claim 2.

12. The method of claim 11, wherein the active substance is a drug.

13. The method of claim 11, wherein the active substance is nicotine.

14. The method of claim 11, wherein the active substance is estradiol.

15. A transdermal system comprising:
   an active substance;
   a backing membrane substantially impermeable to the active substance;
   a reservoir layer comprising:
      the active substance;
      a cyclized polysaccharide selected from the group consisting of cyclodextrin, cyclodextrin polymer, or derivative thereof, at least a part of which is in the form of an inclusion complex formed between the cyclized polysaccharide and the active substance; and
      an agent which regulates controlled dissociation of the inclusion complex within the reservoir, the agent being selected from the group consisting of: excess cyclodextrin, excess free substance, pH adjusting agents, hydrophilic solvents, lipophilic solvents, and mixtures thereof;
      wherein release of the active substance from the transdermal system is regulated by the controlled dissociation of the inclusion complex within the reservoir.

* * * * *